(12) United States Patent
Hirotsu et al.

(10) Patent No.: US 11,725,226 B2
(45) Date of Patent: Aug. 15, 2023

(54) METHOD FOR DETECTING KIDNEY CANCER

(71) Applicants: HIROTSU BIO SCIENCE INC., Chiyoda-ku (JP); NATIONAL UNIVERSITY CORPORATION KUMAMOTO UNIVERSITY, Kumamoto (JP)

(72) Inventors: Takaaki Hirotsu, Tokyo (JP); Hirofumi Jono, Kumamoto (JP)

(73) Assignees: HIROTSU BIO SCIENCE INC., Chiyoda-ku (JP); NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 555 days.

(21) Appl. No.: 16/640,593

(22) PCT Filed: Aug. 20, 2018

(86) PCT No.: PCT/JP2018/030600
§ 371 (c)(1),
(2) Date: Feb. 20, 2020

(87) PCT Pub. No.: WO2019/039415
PCT Pub. Date: Feb. 28, 2019

(65) Prior Publication Data
US 2020/0208192 A1 Jul. 2, 2020

(30) Foreign Application Priority Data
Aug. 21, 2017 (JP) ................................. 2017-158824

(51) Int. Cl.
*G01N 33/574* (2006.01)
*C12Q 1/06* (2006.01)
*G01N 1/38* (2006.01)

(52) U.S. Cl.
CPC ................. *C12Q 1/06* (2013.01); *G01N 1/38* (2013.01); *G01N 33/57438* (2013.01); *G01N 33/57488* (2013.01)

(58) Field of Classification Search
CPC .................. G01N 33/57438; G01N 33/57488
See application file for complete search history.

(56) References Cited

U.S. PATENT DOCUMENTS

2017/0016906 A1 1/2017 Hirotsu et al.

FOREIGN PATENT DOCUMENTS

| EP | 3 654 035 A1 | 5/2020 |
| JP | 6164622 B1 | 7/2017 |
| WO | WO 2015/088039 A1 | 6/2015 |

OTHER PUBLICATIONS

Hirotsu, T. et al. PLOS One, doi.org/10.1371/journal.pone.0118699 (Mar. 11, 2015). (Year: 2015).*

(Continued)

*Primary Examiner* — Diana B Johannsen
(74) *Attorney, Agent, or Firm* — Oblon, McClelland, Maier & Neustadt, L.L.P.

(57) ABSTRACT

The present invention provides a method for highly sensitively and highly specifically detecting a kidney cancer. According to the present invention, there is provided, for example, a method for detecting a kidney cancer in a subject, comprising diluting a urine sample obtained from the subject at a predetermined ratio, and determining whether or not nematodes exhibit attraction behavior toward the diluted urine sample, wherein the predetermined ratio is 200 or more.

8 Claims, 4 Drawing Sheets

(56) References Cited

OTHER PUBLICATIONS

Extended European Search report dated Apr. 26, 2021 in European patent Application No. 18847704.6, 8 pages.
Kazushi Yoshida, et al., "Odour concentration-dependent olfactory preference change in *C. elegans*," Nature Communications, XP055637961, Mar. 13, 2012, 11 pages.
Chunyan Liao, et al., "Behavioural and Genetic Evidence for *C. elegans*' Ability to Detect Volatile Chemicals Associated with Explosives," PLoS ONE, vol. 5, No. 9, XP055286798, Sep. 2010, 9 pages.
International Search Report dated Nov. 20, 2018 in PCT/JP2018/030600 filed Aug. 20, 2018, 1 page.

\* cited by examiner

METHOD FOR DETECTING KIDNEY CANCER

TECHNICAL FIELD

The present invention provides a method for detecting a kidney cancer.

BACKGROUND ART

It was clarified that nematodes exhibit attraction behavior toward urine samples of cancer patients and exhibit avoidance behavior against urine samples of healthy individuals. Based on such tactic behavior of nematodes, a method for diagnosing cancer has been developed (Patent Literature 1). In the evaluation system of this method, a urine sample is diluted about 10-fold. When nematodes exhibit attraction behavior toward the diluted sample, then it can be determined that the subject from which the sample is derived, has a cancer. When the dilution ratio of the sample is high, needless to say, the accuracy of determination greatly decreases (Patent Literature 1).

CITATION LIST

Patent Literature

Patent Literature 1: WO2015/088039

SUMMARY OF INVENTION

The present inventors considered that it is demanded to develop a method for highly sensitively and highly specifically detecting a kidney cancer or a method for highly sensitively and highly specifically detecting a kidney cancer in dialysis patients who are reported to develop a kidney cancer at a high rate.

The present invention provides a method for detecting a kidney cancer.

According to Patent Literature 1 (WO2015/088039), nematodes exhibit attraction behavior toward urine samples obtained from cancer patients; whereas nematodes exhibit avoidance behavior against urine samples obtained from healthy individuals. Particularly, if a urine sample is diluted 10-fold with water, highly sensitive and highly specific detection can be attained; however, as the dilution ratio increases (for example, to a dilution ratio of 100 or more), the detection sensitivity and specificity decrease.

When the present inventors have found that when urine derived from patients having a kidney cancer was diluted at the dilution ratio mentioned above and evaluated in an evaluation system for attraction behavior of nematodes, the detection sensitivity and specificity were low compared to those for other cancers. On the other hand, the present inventors have found that when urine samples derived from patients having a kidney cancer was diluted at a higher ratio (for example, at a dilution ratio of 200 or more, 300 or more, 400 or more, 500 or more, 600 or more, 700 or more, 800 or more, 900 or more or 1,000 or more), and used in the evaluation system, the sensitivity and specificity for detecting a kidney cancer was dramatically improved. The present inventors also have found that cancer patients can be distinguished from patients having a kidney disease by subjecting a urine sample diluted at the higher dilution ratio to the above evaluation system. The present invention has been attained based on these findings.

More specifically, according to the present invention, for example, the following invention is provided.

(1) A method for detecting a kidney cancer in a subject, comprising:
diluting a urine sample obtained from the subject at a predetermined ratio; and
determining whether or not nematodes exhibit attraction behavior toward the diluted urine sample,
wherein the predetermined ratio is a ratio of 200 or more (or 300 or more, 400 or more, 500 or more, 600 or more, 700 or more, 800 or more, 900 or more or 1,000 or more).

(2) The method according to (1), wherein the subject is a subject suspected of having a cancer.

(3) The method according to (1) or (2), wherein the subject is a patient having a kidney disease.

(4) The method according to any one of (1) to (3), wherein the predetermined ratio is a ratio of 500 or more or 1,000 or more.

(5) The method according to (4), wherein the predetermined ratio is a ratio ranging from 1,000 to 20,000.

(6) The method according to any one of (1) to (5), wherein when nematodes exhibit attraction behavior toward the diluted urine sample, then it is determined that a subject from which the urine sample is derived, has a cancer or a possibility thereof; whereas, when nematodes exhibit avoidance behavior, then it is determined that the subject from which the urine sample is derived, does not have a cancer or a possibility thereof.

(7) A diagnostic kit for a kidney cancer comprising nematodes for use in a method for detecting a kidney cancer, comprising:
diluting a urine sample obtained from a subject at a predetermined ratio; and
determining whether or not nematodes exhibit attraction behavior toward the diluted urine sample,
wherein the predetermined ratio is a ratio of 200 or more (or 300 or more, 400 or more, 500 or more, 600 or more, 700 or more, 800 or more, 900 or more or 1,000 or more).

(8) Use of a urine sample obtained from a subject for detecting a kidney cancer in the subject, comprising
diluting the urine sample at a predetermined ratio; and
determining whether or not nematodes exhibit attraction behavior toward the diluted urine sample,
wherein the predetermined ratio is a ratio of 200 or more (or 300 or more, 400 or more, 500 or more, 600 or more, 700 or more, 800 or more, 900 or more or 1,000 or more).

(9) A method for detecting a cancer in a subject, comprising:
diluting a urine sample obtained from the subject at a first predetermined ratio;
diluting the urine sample obtained from the subject at a second predetermined ratio; and
determining whether or not nematodes exhibit attraction behavior toward the diluted urine samples,
wherein the first predetermined ratio is a ratio ranging from 5 to 100 and the second predetermined ratio is a ratio of 200 or more (or 300 or more, 400 or more, 500 or more, 600 or more, 700 or more, 800 or more, 900 or more or 1,000 or more).

(10) The method according to (9), wherein when nematodes exhibit attraction behavior toward the sample diluted at the second predetermined ratio, and the nematodes exhibit avoidance behavior against the sample diluted at the first predetermined ratio, then it is determined that the subject from which the urine sample is derived, has a kidney cancer or a possibility thereof.

(11) The method according to (9), wherein
when nematodes exhibit attraction behavior toward the sample diluted at the first predetermined ratio, and the nematodes exhibit avoidance behavior against the sample diluted at the second predetermined ratio, then it is determined that the subject from which the urine sample is derived, has a cancer except a kidney cancer or a possibility thereof.

(12) A method for improving detection sensitivity or specificity for a kidney cancer in an evaluation system for tactic behavior of nematodes to a urine sample obtained from a subject, comprising diluting the urine sample obtained from the subject at a ratio equal to or more than a predetermined ratio of, for example, 200 or more (or 300 or more, 400 or more, 500 or more, 600 or more, 700 or more, 800 or more, 900 or more or 1,000 or more).

(13) An evaluation system for tactic behavior of nematodes to a urine sample obtained from a subject, comprising: a diluted urine sample obtained from a subject suspected of having a kidney cancer or a patient having a kidney cancer and diluted at a predetermined ratio of 200 or more (or 300 or more, 400 or more, 500 or more, 600 or more, 700 or more, 800 or more, 900 or more or 1,000 or more); and nematodes.

(14) The method according to any one of (1) to (6), the diagnostic kit according to (7), the use according to (8), the method according to any one of (9) to (11), the method according to (12) or the evaluation system according to (13), wherein the cancer is an early-stage cancer.

(15) The method according to any one of (1) to (6), a diagnostic kit according to (7), the use according to (8), the method according to any one of (9) to (11), the method according to (12) or the evaluation system according to (13), wherein the subject is a dialysis patient.

BRIEF DESCRIPTION OF DRAWINGS

FIG. 2A is a graph showing the tactic behavior evaluation results of nematodes when urine samples obtained from patients having a kidney cancer and diluted 100-fold were used. In FIG. 2A, the vertical axis represents a tactic index; whereas the horizontal axis represents sample No. Sample numbers 1 to 19 are arranged sequentially from the left end of the figure.

FIG. 2B is a graph showing the tactic behavior evaluation results of nematodes when urine samples obtained from patients having a kidney cancer and diluted 10-fold were used. In FIG. 2B, the vertical axis represents a tactic index; whereas the horizontal axis represents sample No. Sample numbers 1 to 19 are arranged sequentially from the left end of the figure.

FIG. 3A is a graph showing the tactic behavior evaluation results of nematodes when urine samples obtained from patients having a kidney cancer and diluted 1,000-fold were used. In FIG. 3A, the vertical axis represents a tactic index; whereas the horizontal axis represents sample No. Sample numbers 1 to 19 are arranged sequentially from the left end of the figure.

FIG. 3B is a graph showing the tactic behavior evaluation results of nematodes when urine samples obtained from patients having a kidney cancer and diluted 10,000-fold were used. In FIG. 3B, the vertical axis represents a tactic index; whereas the horizontal axis represents sample No. Sample numbers 1 to 19 are arranged sequentially from the left end of the figure.

DETAILED DESCRIPTION OF THE INVENTION

As used herein, the "nematodes" refer to *Caenorhabditis elegans*. Nematode species is a popular organism raised as a model organism and studied worldwide in biological researches. Nematodes have features of being easily raised and having a good sense of smelling.

As used herein, the "cancer" refers to a cancer such as a kidney cancer, stomach cancer, uterine cancer, liver cancer, breast cancer, colorectal cancer, esophageal cancer, pancreatic cancer, prostate cancer, bile duct cancer, lung cancer, blood cancer, leukemia and lymphoma.

As used herein, the "kidney cancer" refers to a cancer developed in the kidney including renal cell cancer and renal pelvis cancer.

The stages of renal cell cancer can be determined based on the TNM classification shown in Table 1-1.

TABLE 1-1

Stage of renal cell cancer (TNM classification)

| Class | Criteria |
|---|---|
| T1a | Renal cell cancer has a diameter of 4 cm or less and remains within the kidney |
| T1b | Renal cell cancer has a diameter of 4 to 7 cm and remains within the kidney |
| T2a | Renal cell cancer has a diameter of 7 to 10 cm and remains within the kidney |
| T2b | Renal cell cancer has a diameter more than 10 cm and remains within the kidney |
| T3a | Renal cell cancer spreads to the renal vein or peripheral adipose tissue but not beyond the Gerota's fascia* |
| T3b | Renal cell cancer spreads to the large vein under the diaphragm |
| T3b | Renal cell cancer spreads to the large vein above the diaphragm or the vessel wall of the large vein |
| T4 | Renal cell cancer spreads beyond the Gerota's fascia or reaches the adrenal gland |
| N0 | No regional lymph nodes metastasis |
| N1 | Regional lymph node metastasis present (single site) |
| N2 | Regional lymph node metastasis present (two sites or more) |
| M0 | No distant metastasis |
| M1 | Metastasis to distant organs |

*Gerota's fascia: membrane covering the kidney

Further, the stages of a kidney cancer can be determined based on the following Table 1-2.

TABLE 1-2

Stage of renal cell cancer

|  | N0 and M0 | N1 and M0 | N2 and M1 |
|---|---|---|---|
| T1 | Stage I | Stage III | Stage IV |
| T2 | Stage II | Stage III | Stage IV |
| T3 | Stage III | Stage III | Stage IV |
| T4 | Stage IV | Stage IV | Stage IV |

The stage (any one of stages I, II, III and IV) of renal pelvis/ureter cancer can be determined based on, e.g., "General Rule for Clinical and Pathological Studies on Renal Pelvic, Ureteral and Bladder Cancer" edited by the Japanese Urological Association/the Japanese Society of Pathology/ the Japan Radiological Society, April, 2011, first edition (KANEHARA & Co., LTD.).

As used herein, the "kidney disease" refers to a disease or a disease state caused by hypofunction of the kidney. A kidney disease is caused basically when the glomerulus and tubule of the kidney are damaged.

The function of the kidney once damaged is not recovered in most cases, and a pathological condition called a chronic kidney disease or chronic renal failure is developed.

The chronic kidney disease is defined as the disease state where, for example, one or both of the following states (1) and (2) continue for 3 months or more:

(1) the presence of a kidney disorder is apparently observed by urinalysis, diagnostic imaging, blood test and pathology, particularly proteinuria of 0.15 g/gCr or more (albuminuria of 30 mg/gCr or more) is observed;

(2) the estimated glomerular filtration rate (eGFR) decreases to less than 60 (mL/min/1.73 m$^2$).

The eGFR of a man can be calculated based on the following expression:

$$eGFR\ (mL/min/1.73\ m^2) = 194 \times serum\ creatinine\ level\ (mg/dL)^{-1.094} \times age^{-0.287}$$

The eGFR of a woman is obtained by multiplying the eGFR of a man by 0.739.

The severity of a kidney disease can be evaluated further based on the estimated glomerular filtration rate.

TABLE 2

| Severity of chronic kidney disease (CDK staging) | |
| --- | --- |
| Severity (CDK stage) | Criteria |
| Stage 1 (normal) | eGFR value: 90 or more |
| Stage 2 (normal or mildly decreased) | eGFR value: ≤60 to <90 |
| Stage 3a (mildly to moderately decreased) | eFGR value: ≤45 to <60 |
| Stage 3b (moderately to severely decreased) | eGFR value: ≤30 to <45 |
| Stage 4 (severely decreased) | eGFR value: ≤15 to <30 |
| Stage 5 (last-stage kidney failure) | eGFR value: <15 |

As used herein, the "subject" refers to a mammal, for example, a human. If the subject is a human, the subject is sometimes called as a patient. The subject may be a subject having a cancer or a subject suspected of having a cancer (hereinafter sometimes referred to simply as a "subject suspected of having a cancer").

As used herein, "about" means that the range plus or minus 10% or 5% of the numerical value following "about" is included.

As used herein, the "tactic behavior" refers to attraction behavior or avoidance behavior. The attraction behavior refers to an action to reduce the physical distance from a certain substance; whereas the avoidance behavior is an action to increase the physical distance from a certain substance. The substance inducing the attraction behavior is referred to as an attractant; whereas the substance inducing the avoidance behavior is referred to as a repellent.

Nematodes (C. elegans) are inherently attracted by an attractant and escape from a repellent by sensing smell. The action to migrate towards an attractant is referred to as attraction behavior; whereas the action to escape from a repellent is referred to as avoidance behavior. The attraction behavior and the avoidance behavior are collectively referred to as tactic behavior. Nematodes exhibit attraction behavior toward urine samples from cancer patients and avoidance behavior against urine samples from healthy individuals.

As used herein, the "method for detecting a cancer" and analogous expressions may be rephrased by a "method for obtaining preliminary information about the presence or absence of a cancer", a "method for obtaining preliminary information for diagnosing a cancer", a "preliminary method for diagnosing a cancer", a "method for detecting possibility of cancer" or a "method for detecting cancer cells". In the present specification, the method for detecting a cancer may have industrial availability.

[1] According to the present invention, there is provided a method for detecting a kidney cancer in a subject, comprising:

(1) diluting a urine sample obtained from the subject at a predetermined ratio; and (2) determining whether or not nematodes exhibit attraction behavior toward the diluted urine sample, wherein the predetermined ratio is a ratio of 200 or more (or 300 or more, 400 or more, 500 or more, 600 or more, 700 or more, 800 or more, 900 or more or 1,000 or more).

In the present invention, the subject may be a human. In the present invention, the subject may be a patient affected with a kidney disease (for example, chronic kidney disease). In the present invention, the subject may be, for example, a subject suspected of having a cancer or a subject having a cancer (for example, cancer except a kidney cancer or a kidney cancer). In an embodiment of the present invention, the subject may be a subject having a kidney disease. In an embodiment of the present invention, the subject may be a subject having a kidney disease and suspected of having a cancer. In an embodiment of the present invention, the subject may be a subject having a cancer except a kidney cancer and a kidney disease. In an embodiment of the present invention, the subject may be a subject having a kidney cancer and a kidney disease. In an embodiment of the present invention, the subject may be a subject receiving dialysis. In an embodiment of the present invention, the subject may be a patient having a chronic kidney disease having a CDK stage selected from the group consisting of 1, 2, 3a, 3b, 4 and 5. In the present invention, a kidney cancer of a patient having a chronic kidney disease can be detected even if the disease is in any one of CDK stages.

In the present invention, the kidney cancer to be detected is cancer selected from cancers at stage I, II, III and IV. The method of the present invention is suitable for detecting any one of the cancers at stage I, II, III and IV; however, the method is suitable for an early-stage cancer (i.e., stage-I cancer and stage-II cancer), and more specifically, suitable for detecting a stage-I kidney cancer.

In the present invention, the predetermined ratio may be a ratio of, for example, beyond 100, such as 200 or more, 300 or more, 400 or more, 500 or more, 600 or more, 700 or more, 800 or more, 900 or more, 1000 or more, 2000 or more, 3000 or more, 4000 or more, 5000 or more, 6000 or more, 7000 or more, 8000 or more, 9000 or more or 10000 or more. In the present invention, the predetermined ratio, although it is not particularly limited, may be a ratio of, for example, a ratio of 100000 or less, a ratio of 50000 or less, a ratio of 40000 or less, a ratio of 30000 or less, a ratio of 20000 or less, a ratio of 19000 or less, a ratio of 18000 or less, a ratio of 17000 or less, a ratio of 16000 or less, a ratio of 15000 or less, a ratio of 14000 or less, a ratio of 13000 or less, a ratio of 12000 or less, a ratio of 11000 or less or a ratio of 10000 or less. In the present invention, the predetermined ratio, although it is not particularly limited, may be a ratio ranging from, for example, a ratio ranging from 200 to 50000, a ratio ranging from 200 to 40000, a ratio ranging from 200 to 30000, a ratio ranging from 200 to 20000, a ratio ranging from 500 to 20000, a ratio ranging from 500 to 15000, a ratio ranging from 5000 to 15000, a ratio ranging from 500 to 30000, a ratio ranging from 500 to 50000, a ratio ranging from 2000 to 50000, a ratio ranging from 3000 to 50000, a ratio ranging from 4000 to 50000, a ratio ranging from 5000 to 50000, a ratio ranging from 5000 to 30000 or a ratio ranging from 1000 to 10000. In a specific embodiment, the predetermined ratio may be, for example, about 1000, about 2000, about 3000, about 4000, about 5000, about 6000, about 7000, about 8000, about 9000, about 10000, about 11000, about 12000, about 13000, about 14000, about 15000, about 16000, about 17000, about 18000, about 19000 or about 20000.

In an embodiment of the present invention, a plurality of predetermined ratios falling within the aforementioned range can be employed as the predetermined ratio (for example, in the above [1] (1), dilution series can be employed). The dilution series may be prepared from any one of a plurality of predetermined ratios, such as a dilution series of 2- to 20-fold, a dilution series ranging from 5- to 10-fold or a dilution series of 10-fold.

In the present invention, a urine sample may be diluted with a solvent such as water, distilled water or sterile water.

Whether or not nematodes exhibit attraction behavior toward a urine sample can be determined by observing nematodes' behavior, i.e., moving closer to or away from a urine sample placed at a predetermined distance (for example, 1 cm to 5 cm) from the nematodes. When some of nematodes moved closer to the urine sample and others moved away from the urine sample, if the ratio of nematodes moving closer to the urine sample is higher than that of nematodes moving away from the urine sample, it can be determined that nematodes exhibit attraction behavior toward a test sample. In contrast, if the ratio of nematodes moving closer to the urine sample is lower than that of nematodes moving away from the urine sample, it can be determined that nematodes exhibit avoidance behavior against the urine sample.

Alternatively, a tactic index is obtained in accordance with, e.g., the following expression. Based on the index, whether nematodes exhibit attraction behavior or avoidance behavior may be determined.

Tactic Index (Tactic index)={(number of nematodes individuals moved closer to urine sample)−(number of nematodes individuals moved away from urine sample)}/total number of nematodes individuals The tactic index is a numerical value ranging from −1 to +1. When attraction behavior is exhibited, the index results in a positive value; whereas when avoidance behavior is exhibited, the index results in a negative value. It can be interpreted that the larger the absolute value of the tactic index, the more distinctive the tactic behavior.

According to an embodiment, the method of the present invention may further comprise (3) determining whether the urine sample is an attractant or a repellent based on the tactic behavior of nematodes to a test sample.

In the method of the present invention, if nematodes exhibit attraction behavior toward a urine sample, then it is determined that the subject has a kidney cancer or a possibility thereof. In the method of the present invention, for example, if nematodes exhibit avoidance behavior against a urine sample, then it is determined that the subject does not have a kidney cancer or a possibility thereof.

In the present invention, tactic behavior of nematodes to samples diluted at different predetermined ratios can be evaluated. More specifically, according to the present invention, there is provided a method for detecting a cancer in a subject, comprising:

diluting a urine sample obtained from the subject at a first predetermined ratio;

diluting the urine sample obtained from the subject at a second predetermined ratio; and determining whether or not nematodes exhibit attraction behavior toward the diluted urine samples, wherein the first predetermined ratio is a ratio ranging from 5 to 100, and the second predetermined second ratio is a ratio of 200 or more (or 300 or more, 400 or more, 500 or more, 600 or more, 700 or more, 800 or more, 900 or more or 1,000 or more).

According to Patent Literature 1, cancers except a kidney cancer are widely detected based on tactic behavior of nematodes. The tactic behavior of nematodes can be most highly sensitively and highly specifically determined by diluting a urine-sample 5- to 100-fold, preferably about 10-fold. In contrast, according to the present invention, a cancer of the kidney, which is an organ producing urine, can be highly sensitively and highly specifically determined at a predetermined ratio of 200 or more (or 300 or more, 400 or more, 500 or more, 600 or more, 700 or more, 800 or more, 900 or more or 1,000 or more). Accordingly, urine derived from a predetermined subject is diluted at a first predetermined ratio to prepare a sample and urine derived from the predetermined subject is diluted at a second predetermined ratio to prepare a sample. Then, tactic behavior of nematodes to each of the samples is evaluated. In this manner, it is determined that the subject has a kidney cancer or that the subject has a non-kidney cancer (i.e., cancer except a kidney cancer).

The second predetermined ratio is a ratio, for example, more than 100 similarly to the predetermined ratio described in the above [1]. More specifically, the ratio may be a ratio of, for example, 200 or more, 300 or more, 400 or more, 500 or more, 600 or more, 700 or more, 800 or more, 900 or more, 1000 or more, 2000 or more, 3000 or more, 4000 or more, 5000 or more, 6000 or more, 7000 or more, 8000 or more, 9000 or more or 10000 or more. In the present invention, the predetermined ratio, although it is not particularly limited, may be a ratio of, for example, a ratio of 50000 or less, a ratio of 40000 or less, a ratio of 30000 or less, a ratio of 20000 or less, a ratio of 19000 or less, a ratio of 18000 or less, a ratio of 17000 or less, a ratio of 16000 or less, a ratio of 15000 or less, a ratio of 14000 or less, a ratio of 13000 or less, a ratio of 12000 or less, a ratio of 11000 or less or a ratio of 10000 or less. In the present invention, the predetermined ratio, although it is not particularly limited, may be a ratio ranging from, for example, a ratio ranging from 200 to 50000, a ratio ranging from 200 to 40000, a ratio ranging from 200 to 30000, a ratio ranging from 200 to 20000, a ratio ranging from 500 to 20000, a ratio ranging from 500 to 15000, a ratio ranging from 500 to 30000, a ratio ranging from 500 to 50000, a ratio ranging from 2000 to 50000, a ratio ranging from 3000 to 50000, a ratio ranging from 4000 to 50000, a ratio ranging from 5000 to 50000, a ratio ranging from 5000 to 30000 or a ratio ranging from 1000 to 10000. In a specific embodiment, the predetermined ratio may be, for example, about 1000, about 2000, about 3000, about 4000, about 5000, about 6000, about 7000, about 8000, about 9000, about 10000, about 11000, about 12000, about 13000, about 14000, about 15000, about 16000, about 17000, about 18000, about 19000 or about 20000. As described above, dilution series may be prepared and put in use.

For example, if nematodes exhibit attraction behavior toward a sample derived from the urine of a predetermined subject and diluted at a first predetermined ratio, then it can be determined that the subject has a cancer except a kidney cancer or a possibility thereof. In contrast, if nematodes exhibit attraction behavior toward a sample derived from the urine of the predetermined subject and diluted at a second predetermined ratio, then it can be determined that the subject has a kidney cancer or a possibility thereof. For example, if nematodes exhibit attraction behavior toward a sample derived from the urine of a predetermined subject and diluted at a first predetermined ratio and avoidance behavior against a sample derived from the urine of the predetermined subject and diluted at a second predetermined ratio, then it can be determined that the subject has a cancer except a kidney cancer or a possibility thereof. For example, if nematodes exhibit attraction behavior toward a sample derived from the urine of a predetermined subject and diluted at a second predetermined ratio and avoidance behavior against a sample derived from the urine of the predetermined subject and diluted at a first predetermined ratio, then it can be determined that the subject has a kidney cancer or a possibility thereof. The subject, diluting solvent, method for evaluating tactic behavior and method for detecting a cancer are the same as defined above.

According to the present invention, there is provided a diagnostic kit for a kidney cancer, containing nematodes, the kit being for use in a method for detecting a kidney cancer, the method including:

diluting a urine sample obtained from a subject at a predetermined ratio; and determining whether or not nematodes exhibit attraction behavior toward the diluted urine sample, wherein the predetermined ratio is a ratio of 200 or more (or 300 or more, 400 or more, 500 or more, 600 or more, 700 or more, 800 or more, 900 or more or 1,000 or more). The subject, diluting solvent, method for evaluating tactic behavior and method for detecting a cancer are the same as defined above. The predetermined ratio can be set at the same as the predetermined ratio described in the above [1] or the second predetermined ratio.

According to the present invention, there is provided a diagnostic kit for a kidney cancer containing nematodes, the kit being for use in the method for detecting a kidney cancer according to the present invention. The subject, diluting solvent, method for evaluating tactic behavior and method for detecting a cancer are the same as defined above.

According to the present invention, there is provided use of a urine sample obtained from a subject for use in detecting a kidney cancer in the subject, comprising:

diluting the urine sample at a predetermined ratio; and determining whether or not nematodes exhibit attraction behavior toward the diluted urine sample, wherein the predetermined ratio is a ratio of 200 or more (or 300 or more, 400 or more, 500 or more, 600 or more, 700 or more, 800 or more, 900 or more or 1,000 or more). The subject, diluting solvent, method for evaluating tactic behavior and method for detecting a cancer are the same as defined above. The predetermined ratio can be set at the same as the predetermined ratio described in the above [1] or the second predetermined ratio.

According to the present invention, there is provided a method for improving detection sensitivity or specificity for a kidney cancer in an evaluation system for tactic behavior of nematodes to a urine sample obtained from a subject, wherein the urine sample obtained from the subject is diluted 200-fold or more (or 300-fold or more, 400-fold or more, 500-fold or more, 600-fold or more, 700-fold or more, 800-fold or more, 900-fold or more or 1,000-fold or more). The subject, diluting solvent, method for evaluating tactic behavior and method for detecting a cancer are the same as defined above. The dilution ratio can be set at the same as the predetermined ratio described in the above [1] or the second predetermined ratio.

According to the present invention, there is also provided an evaluation system for tactic behavior of nematodes to a urine sample obtained from a subject, comprising: a urine sample obtained from a subject suspected of having a kidney cancer or a kidney cancer patient and diluted at a dilution ratio of 200 or more (or 300 or more, 400 or more, 500 or more, 600 or more, 700 or more, 800 or more, 900 or more or 1,000 or more); and nematodes. The subject, diluting solvent, method for evaluating tactic behavior and method for detecting a cancer are the same as defined above. The dilution ratio can be set at the same as the predetermined ratio described in the above [1] or the second predetermined ratio.

As used herein, the "method for detecting a cancer" may further include treating a cancer with a suitable cancer therapy. According to the present invention, there is provided a method for treating a kidney cancer, including detecting a kidney cancer by the detection method of the present invention and treating the kidney cancer in the subject in which the kidney cancer is detected. A kidney cancer can be treated by a cancer therapy (for example, administration of an anticancer drug, radiation therapy, immunotherapy to a kidney cancer, or surgical resection thereof) suitable for a kidney cancer.

Now, the present invention will be described by way of Examples; however, Examples are just examples and should not be construed as limiting the scope of the invention.

EXAMPLES

Example 1: Urinalysis Using Nematodes in Patient Having a Kidney Cancer or a Kidney Disease In patients having a kidney disease, the amount of urine is low and also abnormality in urine is sometimes found. In the patients having a kidney disease receiving dialysis, the rate of developing cancer is high. In this example, tests were made as to whether a cancer can be determined based on olfactory perception of nematodes and as to whether a cancer is diagnostically distinguished from a kidney disease.

First, urine samples were obtained from 19 patients having a kidney disease (of them, 10 patients had a kidney cancer, 2 patients received dialysis and a single patient had eosinophilic adenoma). The patients having a kidney cancer, which were all diagnosed as a kidney cancer by doctor, had stage-I kidney cancer having a tumor size (in a specimen) of pT1a (4 cm or less as a primary tumor) in the TNM classification. The detail information about the patients are shown in following Table 3.

TABLE 3

CDK stage and tumor size of test patient

| | |
|---|---|
| CDK stage 1 | tumor size pT1: 2 cases |
| CDK stage 2 | tumor size pT1: 3 cases |
| CDK stage 3a | tumor size pT1: 3 cases |
| CDK stage 3b | tumor size pT1: 1 case |

TABLE 3-continued

CDK stage and tumor size of test patient

| | |
|---|---|
| CDK stage 3b | eosinophilic adenoma: 1 case |
| CDK stage 3b | tumor was not detected: 1 case |
| CDK stage 4 | tumor size pT1: 1 case |
| CDK stage 4 | tumor was not detected: 2 cases |
| CDK stage 5 | tumor was not detected: 3 cases |
| Dialysis patients | tumor was not detected: 2 cases |

Figure 1:
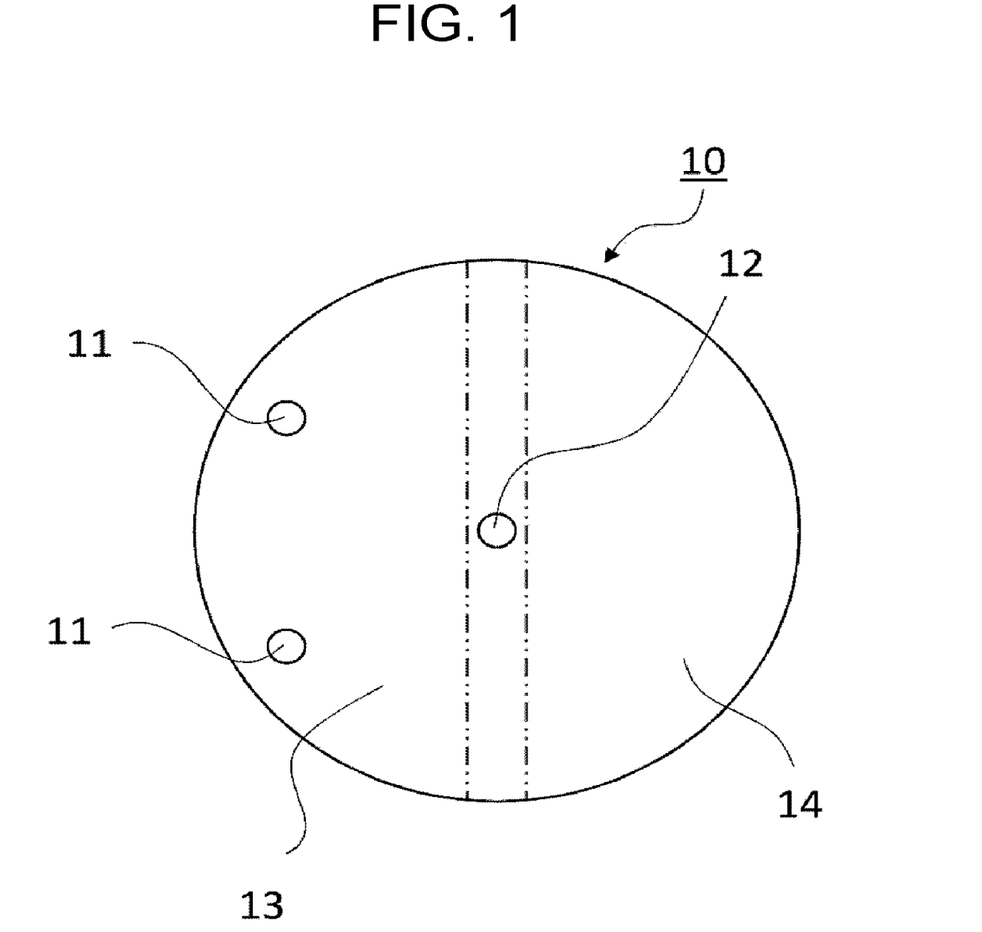
FIG. 1 shows a schematic diagram of the evaluation system for determining tactic behavior of nematodes, carried out in Example 1. In this evaluation system, tactic behavior of nematodes on agar medium contained in a petri dish to a urine sample was determined.

As shown in FIG. 1, a urine sample was diluted 100-fold with sterile water. The diluted urine sample was applied on a marginal portion 11 on a flat-surface agar plate 10, nematodes were applied at the center 12 of the agar plate. Whether nematodes exhibit attraction behavior toward or avoidance behavior against the urine sample was observed. Whether nematodes exhibit attraction behavior or avoidance behavior was determined based on the following tactic index.

Tactic Index (Tactic index)={(number of nematodes individuals in region 13)−(number of nematodes individuals in region 14)}/total number of nematodes individuals wherein region 13 in one of the three regions in the agar plate 10 divided by two dash-dot-dot-dash lines and close to the urine sample; whereas, region 14 is one of the three regions distant from urine sample.

Figure 2A:
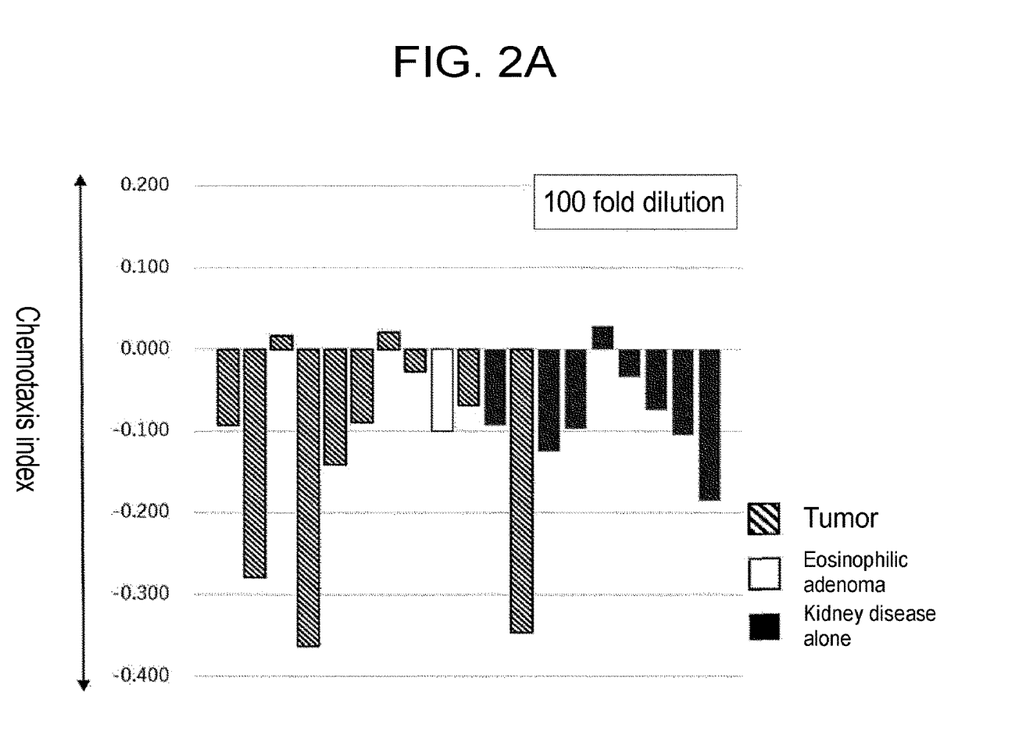
Figure 2B:
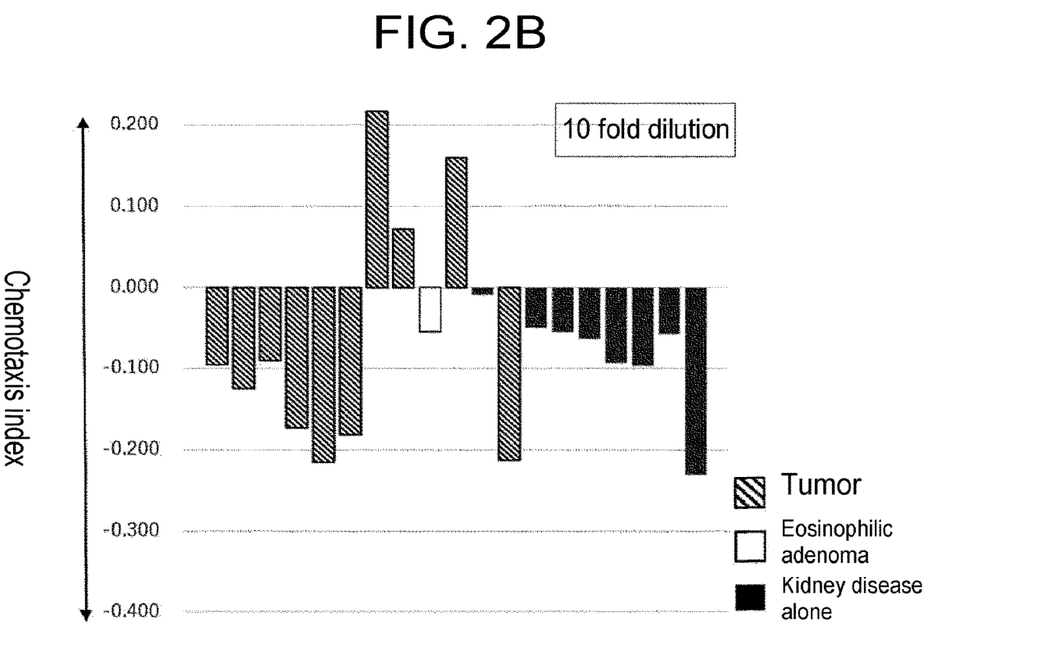

The results were as shown in FIGS. 2A and 2B.

As shown in FIG. 2A, nematodes exhibited attraction behavior toward some of the urine samples (100-fold dilution) derived from cancer patients. Cancer was successfully detected. In contrast, nematodes exhibited avoidance behavior against all of the urine samples of patients having a kidney disease alone. However, as shown in FIG. 2B, nematodes exhibited attraction behavior toward some of the urine samples (10-fold dilution) derived from cancer patients, but the behavior was less distinctive. As shown in FIG. 2A, the urine samples (100-fold dilution), which failed to induce attraction behavior of nematodes, were outstanding.

Figure 3A:
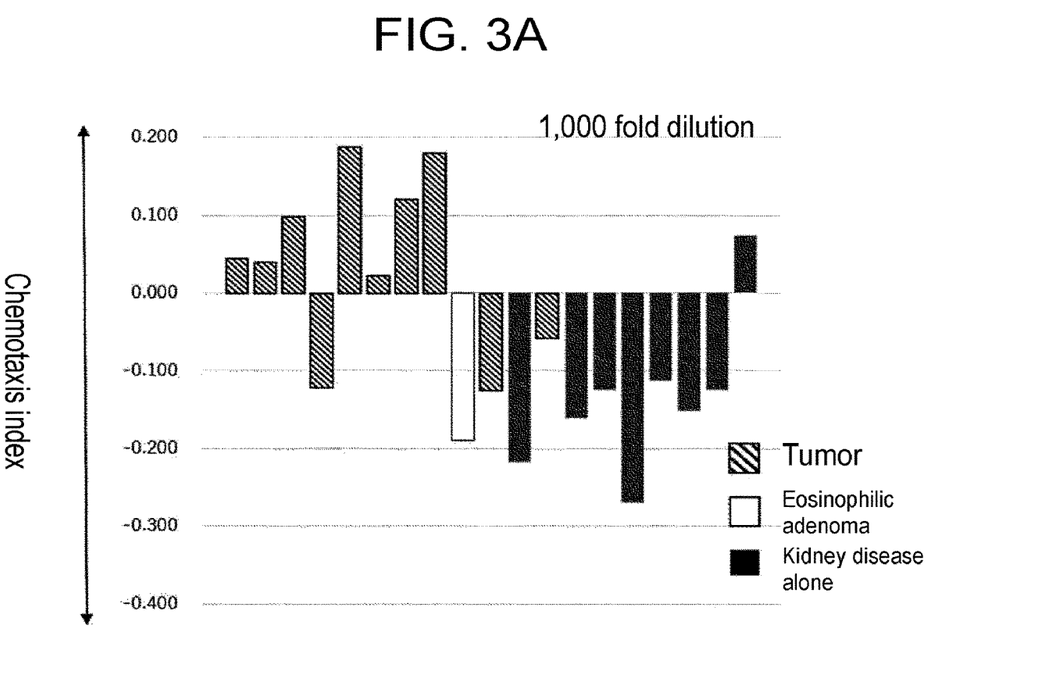
Figure 3B:
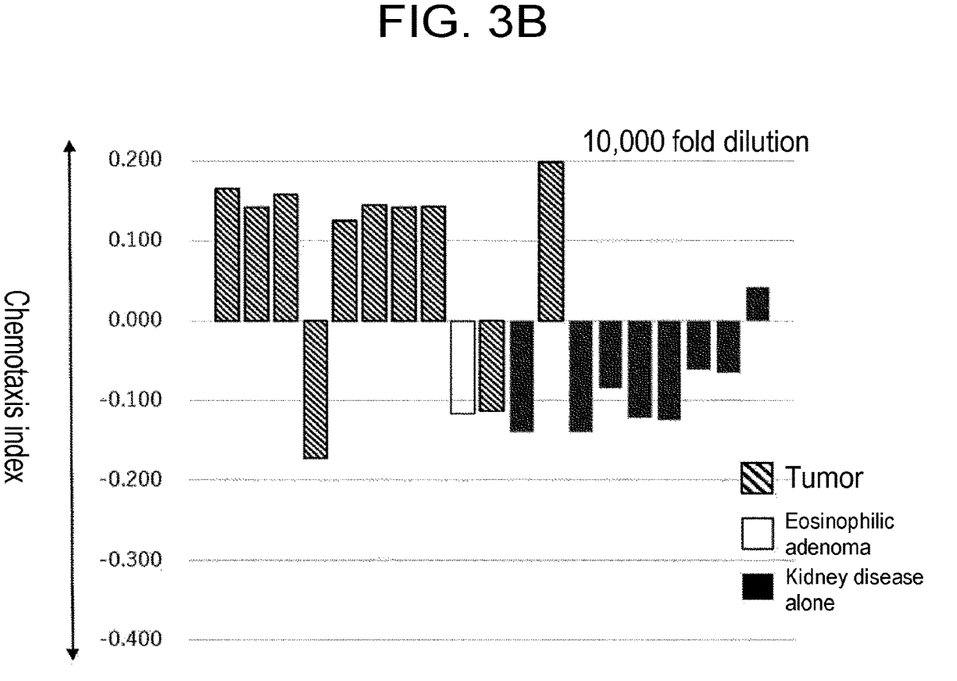

The same urinalysis as above was carried out by varying the dilution ratios of the urine samples. FIGS. 3A and 3B show the urinalysis results obtained in urine samples diluted 1,000-fold and 10,000-fold.

As shown in FIG. 3A, in the urinalysis using urine samples diluted 1,000-fold, nematodes exhibited attraction behavior toward a large number of samples of urine derived from cancer patients. As shown in FIG. 3B, in the urinalysis using urine samples diluted 10,000-fold, nematodes exhibited attraction behavior toward a larger number of samples of urine derived from cancer patients. As shown in FIG. 3B, in the urinalysis using urine samples diluted 10,000-fold, attraction behavior toward a plurality of samples were stably and distinctively detected. Also, as shown in FIGS. 3A and 3B, avoidance behavior against a plurality of samples of urine derived from patients having a kidney disease was stably and distinctively detected.

As is obvious from Table 3, patients in different stages of chronic kidney disease (CKD) were included as test subjects in this time. As shown in FIGS. 3A and 3B, it was not observed that the CKD stages of test subjects influence diagnosis of a kidney cancer. Note that, in FIG. 3B, the 4th sample from the left was derived from a CDK stage-2 patient; the 10th sample from the left was derived from a CDK stage-3b patient.

From Examples of the present invention, it was clearly demonstrated that detection sensitivity and specificity of a cancer are improved by increasing the dilution ratio of a urine sample (in other words, by thinning a urine sample). It was also demonstrated that nematodes stably and distinctively exhibit avoidance behavior against a plurality of samples of urine derived from patients having a kidney disease under the same conditions for dilution ratios. As described in the above, in the evaluation system using tactic behavior of nematodes, kidney cancer patients can be highly sensitively and highly specifically detected by highly diluting a urine sample. Also, in the evaluation system using tactic behavior of nematodes, patients having a kidney cancer (for example, No. 18) can be distinguished from patients having a kidney disease. Further, eosinophilic adenoma (No. 9) can be distinguished from a cancer in the evaluation system of the present invention.

Dialysis patients are known to have a high incidence of cancer compared to non-dialysis patients. From the results of the invention, it was suggested that urinalysis using nematodes can be used for monitoring development of a cancer in dialysis patients. Since pT1a or stage I kidney cancer can be diagnosed by the method of the present invention, it was found that the method of the present invention is useful for early diagnosis of a kidney cancer. In particular, since dialysis patients are reported to develop a cancer at a high rate, the method of the invention can open the way for early diagnosis of a kidney cancer by urinalysis in the dialysis patients.

Nematodes sometimes exhibit avoidance behavior against an attractant if the smell of an attractant is excessively strong (see, for example, Yoshida et al., Nature Communication, 2012 and Taniguchi et al., Science Signaling, 2014). Since the urine derived from a kidney cancer patient contains a cancer-derived component in a high concentration, it is conceivable that avoidance behavior may be induced by a urine sample not highly diluted. It is considered that satisfactory detection can be made at a dilution ratio (e.g., 1,000- to 10,000-fold dilution) higher than a conventional ratio (10- to 100-fold).

The invention claimed is:

1. A method for determining whether a subject having a chronic kidney disease has a kidney cancer or a possibility thereof, the method comprising:
   diluting a urine sample obtained from the subject at 200-fold or more, thereby obtaining a diluted urine sample;
   placing nematodes at a predetermined distance from the diluted urine sample; and
   determining that the subject has a kidney cancer or a possibility thereof when the nematodes exhibit attraction behavior toward the diluted urine sample, or that the subject does not have a kidney cancer or a possibility thereof when the nematodes exhibit avoidance behavior against the diluted urine sample.

2. The method according to claim 1, wherein in the diluting, the urine sample obtained from the subject is diluted at 500-fold or more.

3. The method according to claim 2, wherein in the diluting, the urine sample obtained from the subject is diluted at 1,000-fold to 20,000-fold.

4. A method for determining whether a subject having a chronic kidney disease has a cancer or a possibility thereof, the method comprising:
   diluting a urine sample obtained from the subject at 5-fold to 100-fold, thereby obtaining a first urine sample;

diluting the urine sample obtained from the subject at 200-fold or more, thereby obtaining a second urine sample;

placing nematodes at a predetermined distance from each of the first and second urine samples; and determining that the subject has a kidney cancer or possibility thereof when the nematodes exhibit attraction behavior toward the second urine sample and avoidance behavior against the first urine sample, or that the subject has a cancer other than a kidney cancer or a possibility thereof when the nematodes exhibit attraction behavior toward the first urine sample and avoidance behavior against the second urine sample.

5. The method according to claim 1, wherein the kidney cancer is an early-stage kidney cancer.

6. The method according to claim 1, wherein the subject is receiving dialysis.

7. The method according to claim 1, wherein the predetermined distance is from 1 cm to 5 cm from the diluted urine sample.

8. The method according to claim 4, wherein the predetermined distance is from 1 cm to 5 cm from each of the first and second urine samples.

\* \* \* \* \*